United States Patent [19]

Keith et al.

[11] Patent Number: 5,093,245

[45] Date of Patent: Mar. 3, 1992

[54] LABELING BY SIMULTANEOUS LIGATION AND RESTRICTION

[75] Inventors: Douglas H. Keith, Oakland; Mel N. Kronick, Palo Alto; Lincoln J. McBride, Redwood City; Norman M. Whiteley, San Carlos, all of Calif.

[73] Assignee: Applied Biosystems, Foster City, Calif.

[21] Appl. No.: 148,757

[22] Filed: Jan. 26, 1988

[51] Int. Cl.$^5$ .......................... C12P 19/34; C12Q 1/68; C12Q 1/16; C07H 15/12

[52] U.S. Cl. .......................................... 435/91; 435/6; 435/35; 435/810; 536/27

[58] Field of Search ....................... 435/6, 91, 35, 810; 536/27

[56] References Cited

U.S. PATENT DOCUMENTS 4,775,619  10/1988  Urdea ..................................... 435/6

FOREIGN PATENT DOCUMENTS 0130515  6/1984  European Pat. Off. .
0185494  12/1985  European Pat. Off. .
0246864  5/1987  European Pat. Off. .

OTHER PUBLICATIONS

Ann-Christine Syvanen et al., "Fast Quantification of Nucleic Acid Hybrids by Affinity-based Hybrid Collection", *Nuc. Acids Res.* (1986) 14(12):5037-5048.

H. B. Gamper et al., "Reverse Southern Hybridization", *Nuc. Acids Res.* (1986) 14(24):9943-9954.

T. Goldkorn and D. J. Prockop, "A Simple and Efficient Enzymatic Method for Covalent Attachment of DNA to Cellulose, Application for Hybridization-Restriction Analysis and for in vitro Synthesis of DNA Probes", *Nuc. Acids Res.* (1986) 14(22):9171-9191.

A. C. Forster et al., "Non-radioactive Hybridization Probes Prepared by the Chemical Labelling of DNA and RNA with a Novel Reagent, Photobiotin", *Nuc. Acids Res.* (1985) 13(3):745-761.

J. J. Rossi et al., "An Alternate Method for Synthesis of Double-Stranded DNA Segments", *The J. of Biol. Chem.* (1982) 257(16):9226-9229.

T. Kempe et al., *Nucleic Acids Research*, "Chemical and Enzymatic biotin-labelling of oligodeoxyribonucleotides," vol. 13, No. 1, 1985, pp. 45-57.

R. K. Saiki et al., *Science*, "Enzymatic amplification of beta-globin genomic sequences and restrictions site analysis for diagnosis of sickle cell anemia," vol. 230, Dec., 1985, pp. 1350-1354.

*Primary Examiner*—Robert A. Wax
*Attorney, Agent, or Firm*—Cooley Godward Castro Huddleson & Tatum

[57] ABSTRACT

Termini of restricted double-stranded DNA fragments are modified by ligating the fragments with terminal phosphate-free double-stranded oligonucleotides having a complementary terminus in the presence of a restriction enzyme and a ligase, where joining of the complementary ends results in loss of the restriction enzyme recognition sequence.

12 Claims, No Drawings

LABELING BY SIMULTANEOUS LIGATION AND RESTRICTION

TECHNICAL FIELD

Method for labeling nucleic acid fragments for detection.

BACKGROUND

Today, biology is in many ways the science of proteins and nucleic acids. Nucleic acids are found in all living matter. For each species or host, unique sequences exist providing for the genotype and phenotype of that particular host. Thus, one can use the presence of a particular sequence as indicative of the particular strain or species. In many instances, a number of strains will share a common sequence as distinct from other strains or species, so that one can not only detect a particular strain but, if desired, can detect subspecies, species or genera. In addition, one can distinguish between RNA or DNA so as to determine whether a particular gene is being expressed, the existence of one or more alleles, the level of expression, and the like. Where cells, such as B-cells and T-cells, are involved with genomic rearrangements, one can detect the presence or absence of such rearrangements by employing probes. Thus, the detection of particular nucleic acid sequences is a powerful tool in the diagnosis of disease states, the presence of sets or subsets of cells, the particular strain or species of a pathogen, such as a bacterium, protista, or virus, or the like.

The detection and isolation of sequences is also important in the field of molecular biology. Thus, the use of probes allows for detection of a variety of sequences of interest, including structural genes, regulatory sequences, introns, exons, leader sequences, both translated and untranslated, and the like.

There is also substantial interest in detecting sequences in genetic engineering. Monitoring levels of transcription, detecting the integrity of constructs, monitoring levels of mutation, resection, mapping, or the like provide opportunities for nucleic acid screening and detection.

In many instances, the sequence of interest may be present as only a very small fraction of the total amount of nucleic acid, and/or in very small amount, e.g. attomole levels. Furthermore, the sequence of interest may be accompanied by a number of sequences having substantial homology to the sequence of interest. Thus, relatively high stringencies may be required to ensure the absence of unwanted hetero-duplexing, which may further limit the available concentration of the sequence of interest.

Additionally, the same or similar sequences may appear on nucleic acid fragments of different size and the appearance of a sequence on a particular size fragment may be correlated to the presence of a particular phenotype.

There is also interest in developing analytical systems which can be automated, so as to minimize the time and energy required from technicians, as well as minimizing errors which may result from manual manipulation. In many systems the sample is labeled to allow for detection of the sequence. The labeling can be time consuming and limited as to the nature of the label as in nick translation with radioactive nucleotide triphosphates. In other situations, the particular nature of the label may be limited, as when using terminal deoxytransferase. Other techniques result in random substitution. There is therefore an interest in providing for rapid convenient controlled labeling of sample nucleic acids, where the labeled moiety may be commercially available and require little, if any, technical skills in being used to label the sample.

RELEVANT LITERATURE

Kempe et al., *Nucl. Acids. Res.* (1985) 13:45-57 describe biotinylated oligonucleotides linked to DNA fragments by a ligase. Gamper et al., *Nucl. Acids Res.* (1985) 14:9943-9954, employs a psoralen-functionalized oligomer as a probe which labels target DNA when hybridization and photochemical cross-linking occur. Zapolski et al., *Electrophoresis* (1987) 8:255-261 discuss a robotic system for automating Southern-type nucleic acid hybridization analysis. Goldkorn and Prockop, *Nucl. Acids Res.* (1986) 14:9171-9191 describe techniques for covalent attachment of DNA probes to cellulosic supports for hybridization-restriction analysis. Syvanen et al., *Nucl. Acids Res.* (1986) 14:5037-5048 quantify nucleic acid hybrids by affinity-based hybrid collection. Forster et al., *Nucl. Acids Res.* (1985) 13:745-761 covalently label nucleic acids with biotin photochemically.

SUMMARY OF THE INVENTION

Double-stranded DNA ("dsDNA") fragments are labeled with detectable double-stranded nucleic acid that possesses a terminus complementary to at least one terminus of the double-stranded DNA fragments to be labeled. The labeling double-stranded sequence contains either a label or sequence that can subsequently be detected or isolated. The labeling reaction is performed using ligase to couple the complementary ends and a restriction enzyme to produce the complementary ends on the DNA fragment and to prevent unintended ligation of the fragments to each other. Joining of the nucleic acid labeling segment to the dsDNA fragment results in loss of the restriction enzyme recognition sequence.

DESCRIPTION OF THE SPECIFIC EMBODIMENTS

Methods and compositions are provided for labeling a nucleic acid fragment in a sample. The method involves ligating the label onto the fragment in the presence of a restriction enzyme, where ligation results in loss of the restriction enzyme recognition sequence.

The subject method finds use in a number of situations. One application is in the detection of DNA samples, wherein the probe so labeled serves to link the labeled sample sequence to a solid support. Another situation is in the addition of a particular sequence to restricted sequences, preventing oligomerization of the restricted sequences, while using substantially stoichiometric amounts of the moiety containing the desired sequence. The sequence may be a template or a promoter sequence, a specific sequence for detection or use, for example in the polymerase chain reaction as used in DNA amplification schemes, or the like. Another use is to change the nature of the terminus while removing a restriction site. The labeling procedure would also be useful for labeling DNA restriction fragments which will be sized and detected in order to map regions of DNA.

Usually, the sample employed will be genomic or cDNA involving a plurality of different restricted fragments, generally at least two different fragments, more usually five or more fragments, and may be 50 or more or even thousands or millions of fragments.

The method described above for labeling double-stranded DNA with a ligand using ligation in combination with restriction enzymes is very general and can be used in any procedure where it is desired to covalently attach a ligand to dsDNA. By ligand is intended any moiety of interest, which may be a label allowing for detection, a nucleic acid sequence providing a desired function, a coupling molecule, etc. It is described herein how such a labeling procedure is applied to assays for detection of specific nucleic acid sequences using probes for such sequences. The use of different detectable labels with different colors or fluorescent emission wavelengths would enable the mapping to occur with greater efficiency by using one color attached to a size standard and another one (or more) as samples cut by the same or different restriction enzymes. Hence the ligation/restriction labeling procedure is useful for the production of labeled fragments for any subsequent length analysis.

Alternatively, the same ligation/restriction labeling procedure could be used to add a given oligonucleotide sequence or sequences to the ends of a DNA fragment instead of adding a moiety to be detected. Such an oligonucleotide sequence would prove very valuable, for example, as a primer sequence for DNA or RNA polymerase that would be used to transcribe or reproduce the DNA fragment of interest. In such a fashion, the DNA fragment could be ligated to primers and then amplified by means of a polymerase chain reaction. (Saiki et al., *Science* (1985) 230:1350 ff.) These added defined sequence regions could also be used as a target sequence for a probe used to identify or to pull out the fragment of interest. In this and all other examples of the ligation/restriction procedure the ligated double-stranded pieces added may be synthesized organically, enzymatically, biologically or in some combination of methods.

The use of the subject method will be primarily illustrated in a diagnostic system, where a DNA sample is fragmented using endonuclease cleavage (restriction), followed by labeling.

The source of the sample may be any material or substance comprising nucleic acid. The nucleic acid need not be a naturally occurring nucleic acid, but may be synthesized chemically, enzymatically, or biologically and may have other than naturally occurring purines and pyrimidines. The sample source may be cellular or non-cellular, may be a clinical sample or isolate, may be derived from such physiological media as blood, serum, plasma, stool, pus, scrapings, washings, urine, or the like; may be associated with a set or subset of cells, such as neoplastic cells, lymphocytes, e.g. T-cells or B-cells, monocytes, neutrophils, etc.; pathogens, including viruses, bacteria, mycoplasma, fungi, protozoa, etc.; may include constructs, involving plasmids, viruses or DNA or RNA fragments, or the like. The nucleic acid sample may involve DNA, which may be chromosomal or extrachromosomal, e.g. plasmids, viruses, synthetic constructs, etc. or RNA, such as messenger RNA, transfer RNA, ribosomal RNA, viruses, or the like, where the RNA may be transcribed into dsDNA. The nucleic acid sequences may involve structural genes, untranslated regions, regulatory regions, introns, exons, or the like.

The detection may be for a wide variety of purposes. Detection may involve diagnosis of a diseased state in plant or animal species, such as neoplasia or other aberrant cellular state, the detection of sets or subsets of cells, such as lymphocytes at various stages of differentiation, the detection of strains or species of pathogens, the monitoring of genetic engineering, or the like. Prior to use of the sample in the subject invention, the sample may have been subjected to a variety of chemical or physical treatments, such as proteolysis, extraction, precipitation, separation of nucleic acid from other components, such as lipids, proteins, or the like, hydrolysis of RNA, inactivation of nucleases, concentration, chromatography, dehydration, heating, etc. The sample may be manipulated for a variety of reasons, such as removal of interfering materials, preparation for storage or shipment, concentration, or the like.

The composition will normally be subjected to fragmentation by employing restriction enzymes. The restriction enzymes will cleave in the recognition site, usually having a 4 to 8 bp recognition site. One or more restriction enzymes may be employed where, depending upon the nature of the sample, fragments may be provided varying from 50 bp to 200 kbp or more, more usually from about 0.5 to 25 kbp. Various restriction enzymes may be used resulting in the formation of flush or sticky ends with either 3' or 5' overhangs. In some situations, the presence of sticky ends may be desired as a specific site for linking. For the most part only one restriction enzyme will be used, although in some situations two or more enzymes may be used.

In some instances, the sample may involve the reverse transcription product of messenger RNA, where the mixture may be relatively small sequences of DNA and RNA. If desired, the RNA may be hydrolyzed, leaving only the DNA sequences. In this manner, one would have a composition of solely single-stranded DNA. The single-stranded DNA could then be converted into dsDNA using an enzyme such as DNA polymerase.

Once the sample has been digested or treated in the appropriate manner to provide the desired terminus, the dsDNA may be labeled. The choice of sequence other than the terminus and immediately adjacent nucleotide(s) will generally be arbitrary. The labeling moiety other than the portion of the restriction endonuclease recognition site, e.g. the complementary blunt end, cohesive end or overhang, will usually have at least three base pairs (bp) and may have 50 or more, usually up to about 200 bp or more. The termini of the labeling moiety may lack phosphate, so that the labeling moiety cannot oligomerize, being ligatable solely to the phosphorylated sample.

For the labeling, various compositions may be employed having complementary ends, e.g. short double-stranded sequences, particularly molecules having ends produced by restriction enzymes, either cohesive ends or blunt ends, so as to link to a double-strand and label either one or both strands. The double-stranded sequence could be created from the hybridization of a single pair of oligonucleotides, from the snap-back or hairpin structure of a single oligonucleotide sequence with complementary internal sequences, or even from the hybridization of three or more oliogonucleotides which hybridize to each other in a linear fashion so as to lie next to and across from each other so as to create such a double-stranded sequence. The double-stranded sequences could also be restriction fragments themselves or derivatized restriction fragments possessing termini satisfying the required conditions of sequence and being cohesive to the termini being labeled. By carrying out the ligation of the labeling moiety in the presence of the restriction enzyme, excesses of the labeling moiety may be avoided.

The labeling composition will have usually from one to three oligonucleotide strands. For the most part there will only be two strands, as has been described above. However, three strands provide some flexibility and may find particular application where the restriction enzyme digestion results in a 3' overhang. With three strands, one may employ a bridging strand, and two additional strands, each hybridizing with adjacent portions of the bridging strand, one strand proximal to the 3' end of the bridging strand (the labeling strand) and the other proximal to the 5' end of the bridging strand (the adapter strand). The labeling strand will provide a label or a sequence of interest, e.g. a promoter: the adapter strand will normally abut the strand of the fragment having the same 5'-3' direction and at the other end, the labeling strand.

The adapter strand will have its 5' end phosphorylated and will contain the particular sequence necessary to destroy the recognition site of the restriction enzyme of interest. Upon introduction of the ligase, the labeling strand becomes ligated to the adapter strand and the adapter to the fragment.

By using three strands, one can have a substantially universal sequence where only one strand need be changed for each restriction site. In this way the labeled strand may be kept constant, while only the adapter strand involved in providing the complementary terminus need be changed. The adapter strand which hybridizes to the bridging strand can provide for a cohesive terminus, where the adapter strand is the overhang or where the bridging strand is the overhang, or a flush end to provide for ligation to the fragment.

In a particular example shown below, two oligonucleotides are synthesized, at least one of which contains the label, here a dye, to be added to the nucleic acid samples. The restriction enzyme HindIII has been used in this example to produce fragments with a 5' protruding sticky end.

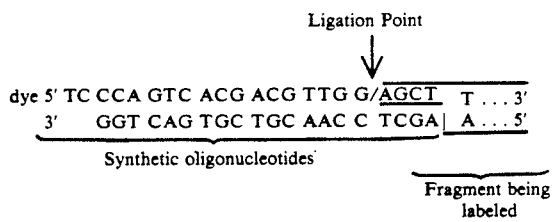

The oligonucleotides are synthesized so as to be complementary to each other and, when hybridized to each other, to have a protruding end complementary to a sticky end of the sample nucleic acid fragment to be labeled. Alternatively, the synthesized oligonucleotides may have a flush end when hybridized to enable ligation to a flush ended fragment. Thus, when a ligating enzyme is added, the labeled oligonucleotide becomes covalently attached to the sample nucleic acid fragment.

The sequence of the oligonucleotides shown in the example above was chosen so that after correct ligation occurs the recognition sequence of the enzyme is destroyed. This choice provides a unique advantage in using ligation labeling: if the cognizant restriction enzyme is present and operational during ligation, then any ligation of sample nucleic acid to itself will be recut. This property yields two significant advantages: first, restriction activity and ligation labeling can occur simultaneously in the same vessel thus minimizing handling and manipulations; second, a large molar excess of the labeling moiety is no longer needed to prevent sample nucleic acid from being ligated to itself. The labeling example shown can be generalized to any restriction enzyme where synthetic oligonucleotides can be ligated into a cleaved restriction enzyme site, where the oligonucleotide contains a sequence that destroys the recognition site of the enzyme. Such a sequence may involve a base change, e.g., from cytosine to thymidine, or perhaps substitution of a derivatized base such as 5-methylcytosine or 3-methyl adenosine, or by substitution of an analog like inosine.

In all examples above and below where restriction enzymes are used for cutting nucleic acid strands at defined recognition sequences, the use of sequence specific DNA cleaving molecules such as natural product analogs, metal ion complexes, peptide fragments, etc. is also possible, e.g. Moser and Dervan, *Science* (1987) 238:645-650.

The labeling need not be direct but may be indirect. That is, the nucleic acid sequence may be modified with a molecule which may then bind to a second molecule which will provide for a detectable signal or other desired property. For example, the nucleic acid sequence may be modified with biotin, where subsequently the nucleic acid sequence may be combined with avidin or streptavidin to which various detectable labels may be conjugated. Alternatively, various ligands may be used other than biotin in conjunction with their naturally occurring receptors or immunoglobulins specific for the ligand.

A wide variety of detectable labels may be used, particularly those which allow for convenient detection. The detection may be as a result of electromagnetic radiation, such as radioactivity, light absorption in the ultraviolet or visible range, fluorescence, or chemiluminescence, enzymes which produce a detectable product or destroy a detectable substrate, stable free radicals, or the like. The various molecules providing for these properties may be joined to the sequence in accordance with conventional ways, either directly or indirectly, depending upon the particular manner of labeling.

As detectable labels, various radioactive elements may be employed, such as $^{32}P$, $^{127}I$, $^{14}C$ $^{3}H$, $^{35}S$; fluorescers, such as fluorescein, rhodamine, phycobiliprotein, rare earth chelates, derivatives thereof, etc., where the fluorescers may be individual molecules or joined in tandem to a nucleic acid or non-(nucleic acid) backbone: enzymes such as horseradish peroxidase, by itself or in conjunction with glucose oxidase, xanthine oxidase, alkaline phosphatase, glucose-6-phosphate dehydrogenase, or the like, usually employing enzymes which react with a substrate to provide a fluorescent or light absorbing product; a member of a specific binding moiety-receptor pair, such as biotin-avidin or streptavidin, or complementary nucleic acid sequences; as well as any other label which provides for detection and can be used in the subject invention.

The following examples are offered by way of illustration and not by way of limitation.

EXPERIMENTAL

Example 1

Use of ligation to label a probe with the ligand biotin.

1. Oligodeoxynucleotides with structures I and II are synthesized on an Applied Biosystem Model 381A DNA synthesizer according to the manufacturer's directions. Structure I is synthesized with C (cytosine) in the X positions shown. The C's are then converted to the structure of X shown by a transamination reaction performed as described by Draper, *Nucleic Acids Research* (1984) 12:988 ff, followed by reaction with long chain arm biotin according to the manufacturer's directions (Pierce Chemical Co., Rockford, Ill.).

2. A reaction mixture is prepared by combining the following reagents:
   1 μl of 1 pmole/μl of pSP64 plasmid (Promega, Madison, Wis.) in 10 mM Tris HCl, 1 mM EDTA, pH 8.0 (TE)
   1 μl of 10× Medium Salt Buffer (Maniatis et al., supra)
   1 μl of 10 mM ATP
   1 μl of 1 unit/μl T4 ligase (Boehringer Mannheim, Indianapolis, Ind.)
   1 μl of biotinylated oligodeoxynucleotide (Structure I containing 2.5 pmole in TE)
   1 μl of complementary oligodeoxynucleotide (Structure II containing 2.5 pmoles in TE)
   3 μl water
   1 μl of 10 units/μl HindIII restriction enzyme (Boehringer Mannheim, Indianapolis, Ind.)

3. The mixture is incubated for 1 hour at 37° C.

4. The reaction is stopped by adding 1 μl of 0.2M EDTA.

purified following the manufacturer's directions. The synthesized sequence is

5' AGC TAC AAC GTC GTG ACT GG 3'

The sequence is chosen so that the first 14 nucleotides (from the 5' end) are complementary to the 3' end of the fluorescein labeled 18-mer and the four nucleotides at the 3' end of the 18 mer are complementary to the 5' sticky end overhang generated by the restriction enzyme HindIII. The particular sequence chosen will destroy the recognition sequence of HindIII when the 18-mer/20-mer duplex is formed and then is ligated to the sticky ends of target DNA that has been cut with the HindIII restriction enzyme.

3. A reaction mixture is prepared by mixing the following reagents:
   1 μg of lambda phage target DNA in 1 μl of TE
   0.9 μl of 10× HindIII reaction buffer (BRL Gaithersberg, Md.)
   3.0 μl of the 18-mer in TE; the number of moles should be twice that of the expected number of sticky ends generated when the HindIII digests the 1 μg of target DNA.
   2.0 μl of the 20-mer in TE; the number of moles should be equal to that of the 18-mer.
   1.0 μl of 10 mM dithiothreitol
   1.0 μl of 3 mM ribose ATP
   0.5 μl of HindIII enzyme (12 units/μl)
   0.5 μl of ligase enzyme (0.5 units)

4. Incubate at 37° C. for 1 hour.

5. Add 0.5 μl of 0.2M EDTA and 1.0 μl of 20 μg/μl glycogen in water.

6. Clean up mixture by performing two phenol/chloroform extractions. Add 10 μl each of phenol and chloroform. Mix and centrifuge. Remove and discard lower phase. Repeat. (Maniatis et al., supra).

Structure I
5' > TXXXTTTTTTTTTTTTTTAGTTATGATGTTGT < 3'

Where X =

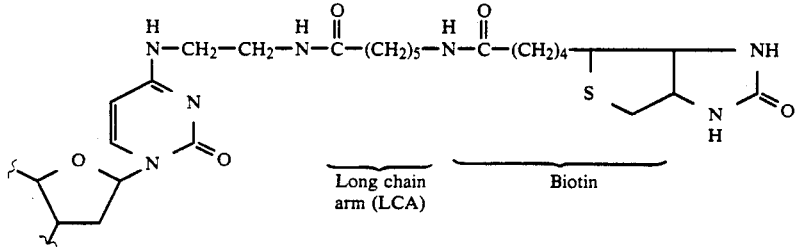

Structure II
5'-AGCTACAACATCATAACT

EXAMPLE 2

Use of ligation to label sample nucleic acid with fluorescent dyes.

Using an Applied Biosystem Model 381 DNA synthesizer, an 18 nucleotide oligomer is synthesized and purified following the manufacturer's directions. The 5' end is terminated with an amino group using Amino-Link TM (Applied Biosystems). This amino group is coupled to fluorescein N-hydroxy succinimide, again according to the manufacturer's directions (Applied Biosystems).

Using an Applied Biosystems Model 381 DNA synthesizer, a 20 nucleotide oligomer is synthesized and 7. Add ≧1 μl 3M NaAc pH 5.5 and 25 μl of 95% ethanol. Mix. Let stand for 30 minutes. Centrifuge.

8. Wash the precipitate with 500 μl of 70% ethanol.

9. Use a vacuum centrifuge to dry sample.

10. Resuspend in 50 μl of 10 mM Tris, 1 mM EDTA, pH 8.0.

11. An aliquot of the reaction mixture is applied to a 0.6% agarose gel run at 3 volts/cm in 1× TBE (Trisborate EDTA) buffer for 4 hours. The fluorescent bands migrating through the gel are detected by an Applied Biosystem 370A DNA sequencer adapted to read horizontal agarose gels. Fluorescent peaks are detected corresponding to the 560, 2027, 2322, 4361, 6557, 9416, and 23,130 base pair fragments in the HindIII cut lambda DNA.

It is evident from the above results that a simple effective process for labeling or modifying termini of double-stranded DNA is provided. Smaller amounts of the labeling moiety are required, while oligomerization of the sample is substantially prevented. Labeling can occur in the same reaction vessel in which restriction or specific fragmentation is accomplished. Thus, a homogeneous product is obtained which provides for accurate sizing, detection and ease of further manipulation.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A method for extending DNA fragments with a ligand comprising:

combining in a reaction mixture said fragments in the simultaneous presence of ligase and a restriction enzyme which cuts in or near the recognition site, with dsDNA comprising said ligand and having a terminus complementary to a terminus of said fragments, wherein said fragments have predetermined termini as a result of digestions with said restriction enzyme, said fragments have terminal phosphates and said complementary termini of said dsDNA lack a terminal phosphate and ligation of said dsDNA results in sequence different from the sequence recognized and cleaved by said restriction enzyme, whereby said fragments and dsDNA are covalently joined.

2. A method according to claim 1, wherein said ligand is a label capable of providing a detectable signal.

3. A method according to claim 1, wherein said ligand is a DNA sequence of interest.

4. A method according to claim 3, including the additional steps of:

selecting a fraction of said covalently joined fragments and dsDNA:

adding to said selected fraction a DNA polymerase, nucleotide triphosphates and sequences complementary to the strands of said dsDNA: and carrying out a polymerase chain reaction to amplify said selected fraction.

5. A method according to claim 4, wherein said selecting is size selection by electrophoresis.

6. A method according to claim 1, wherein said DNA fragments are obtained by adding precursor DNA to be fragmented to said reaction mixture, whereby said precursor DNA is cleaved by said restriction enzyme.

7. A method for labeling DNA fragments with a ligand or radionuclide comprising:

combining said fragments in the simultaneous presence of ligase and a restriction enzyme which cuts in or near the recognition site, with ligand or radionuclide labeled dsDNA of fewer than about 200 bp and having a terminus complementary to a terminus of said fragments, wherein said fragments have predetermined termini as a result of digestion with said restriction enzyme, said fragments have terminal phosphates and said complementary termini of said dsDNA lack a terminal phosphate and ligation of said dsDNA results in a sequence different from the sequence recognized and cleaved by said restriction enzyme, whereby said fragments and dsDNA are covalently joined to label said fragments.

8. A method according to claim 7, wherein said ligand is biotin.

9. A method according to claim 7, wherein said ligand is a radionuclide, fluorescer or an enzyme.

10. A method according to claim 7, wherein said termini have cohesive ends.

11. A method according to claim 7, wherein said fragments are obtained by the step of:

digesting genomic DNA with at least one restriction enzyme to provide fragments of less than about 200 kbp.

12. A labeling composition for binding to a restricted dsDNA fragment resulting in loss of the restriction recognition site by simultaneous restriction and ligation, said composition comprising:

a bridging strand and first and second strands hybridized to said bridging strand, wherein said strands hybridize contiguously to said bridging strand;

said first strand is a labeling strand providing for a double-stranded DNA sequence of interest and a fluorescent label;

said second strand is an adapter strand hybridizing to said bridging strand to provide a cohesive end or blunt end with said bridging strand, and wherein said adapter strand contains a particular sequence necessary to destroy the recognition site of a restriction enzyme of interest.

* * * * *